United States Patent [19]

Wolf et al.

[11] 4,166,186

[45] Aug. 28, 1979

[54] DIHYDROXY CARBAMATES CONTAINING SULPHONIC ACID GROUPS

[75] Inventors: Gerhard D. Wolf; Helmut Engelhard, both of Dormagen; Francis Bentz, Cologne; Günther Nischk, Dormagen, all of Fed. Rep. of Germany

[73] Assignee: Bayer Aktiengesellschaft, Leverkusen, Fed. Rep. of Germany

[21] Appl. No.: 555,229

[22] Filed: Mar. 4, 1975

[30] Foreign Application Priority Data

Mar. 7, 1974 [DE] Fed. Rep. of Germany ....... 2410860

[51] Int. Cl.$^2$ ............................................. C07C 143/155
[52] U.S. Cl. ....................................... 560/27; 560/29; 560/160
[58] Field of Search ............... 260/482 C, 513, 471 C; 560/29, 160, 27

[56] References Cited

U.S. PATENT DOCUMENTS

| | | | |
|---|---|---|---|
| 2,602,059 | 7/1952 | Groote | 260/513 B |
| 3,330,856 | 7/1967 | Broussalian | 260/471 |
| 3,627,822 | 12/1971 | Sundby | 260/513 |
| 3,879,450 | 4/1975 | Velker | 260/513 |

OTHER PUBLICATIONS

Kharasch, J. Org. Chem., 3, pp. 175–192, (1939).

*Primary Examiner*—James O. Thomas, Jr.
*Assistant Examiner*—Michael Shippen
*Attorney, Agent, or Firm*—Gene Harsh; Joseph C. Gil

[57] ABSTRACT

The instant invention relates to dihydroxy carbamates containing sulphonic acid groups, and to a process for their production. They are obtained by the addition of bisulphites to unsaturated carbamates.

2 Claims, No Drawings

DIHYDROXY CARBAMATES CONTAINING SULPHONIC ACID GROUPS

BACKGROUND OF THE INVENTION

It is known that alkali metal hydrogen sulphites can be added to double bonds activated by electron-attracting groups, for example, nitrile or ester groups (cf. R.T.E. Scheneck and J. Danishefsky, J. Org. Chem. 16, 1683 (1951); O. Bayer, Ang. Chem. 61, 233 (1949)). It is also known that bisulphites can be added to aliphatic double bonds which are only weakly activated. It is described for example, in the literature that bisulphites can be added by allyl alcohol (cf. M.S. Kharasch, E.M. May and F.R. Mayo, J. Org. Chem. 3, 175 (1939)). This reaction produced 3-hydroxy propane sulphonic acid in the form of its salts in a yield of only 30%. The yield obtained from the reaction of allyl alcohol and bisulphites was increased (German Pat. No. 915,693), but unfortunately, it was not possible to completely suppress the formation of secondary products, which are assumed to be compounds of the following structure:

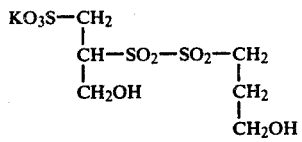

Additionally, complete separation of the inorganic salts formed during reaction from the sulphonate is difficult.

Salts of 3-hydroxy-2-hydroxy methyl propane sulphonic acid are also known. Salts of this kind can be obtained by reacting 2-methylene-1,3-propane diol with bisulphites (DOS 2,224,304). However, 2-methylene-1,3-propane diol can only be obtained at high cost and in small quantities, with the result that the 3-hydroxy-2-hydroxy methyl-1-propane sulphonic acid obtained therefrom cannot be used on a wide scale. In addition, it is relatively difficult to separate this 3-hydroxy-2-hydroxy methyl propane sulphonic acid from the organic salts formed during the reaction. This also applies to the production of 1,4-dihydroxy-2-butane sulphonic acid which may be used for the preparation of stable baths used for copper plating in the absence of an electrical current (DOS 2,132,003).

Accordingly, there is a need for diols containing sulphonate groups which can be produced easily and inexpensively and which, in addition, may be used for a variety of applications by virtue of their favorable properties.

DESCRIPTION OF THE INVENTION

It has now been found that dihydroxy carbamates containing sulphonic acid groups can be obtained by the addition of bisulphites to unsaturated carbamates.

Accordingly, the invention relates to dihydroxy carbamates containing sulphonic acid groups, corresponding to the general formula

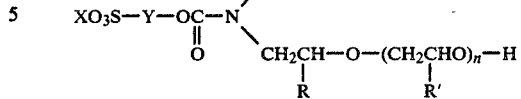

in which
Y — represents a straight-chain for branched $C_{3-6}$ alkylene radical, preferably a propylene radical,
R,R' — represent hydrogen, $C_1$–$C_4$ alkyl or phenyl,
X — represents $NH_4$ or an alkali metal and
n — is a number from 0 to 30, preferably from 0 to 10.

The invention also relates to a process for the production of these compounds which is distinguished by the fact that unsaturated carbamates corresponding to the general formula

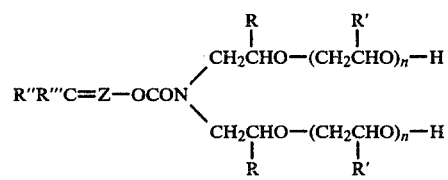

in which
Z — represents a straight-chain or branched $C_2$–$C_4$ alkylene radical, preferably an allyl group,
R" and R''' are the same or different and represent hydrogen or methyl, and
R,R' and n are as defined above, are reacted with bisulphites corresponding to the formula

in which
X — represents $NH_4$ or an alkali metal, in an aqueous medium in the presence of catalytically active oxygen at temperatures of up to 100° C. and at pH-values in the range from 3 to 9, preferably from 7 to 8, the molar ratio of bisulphite to diol being from 1:1 to 5:1.

These dihydroxy sulphonates containing ether groups can be obtained in highly pure form and in very good yields by the method described above. Separation of the inorganic salts formed during the reaction is surprisingly easy and is carried out by extracting the sulphonates with acetone, acetone/water mixtures, chlorinated hydrocarbons, alcohols and alcohol/water mixtures. After extraction, the sulphonates do not contain any salts (even minute quantities could not be detected).

In addition to this easy and quantitative separation of the inorganic salts, another advantage which should be mentioned is the wide scope of application of the compounds according to the invention. They are eminently suitable for use as comonomers for the production of acid-modified polyurethanes and, after they have been reacted, for example with chloroacetic acid (esters), are useful for the production of acid-modified polyamides. The more highly ethoxylated and/or propoxylated derivatives, optionally after they have been reacted with isocyanates, for example, to form diurethanes, are excellent antistatic agents and are used as additives in the production of antistatically finished films, sheets and filaments of polyacrylonitrile or polyamide.

The unsaturated diols used as reactants correspond to the general formula

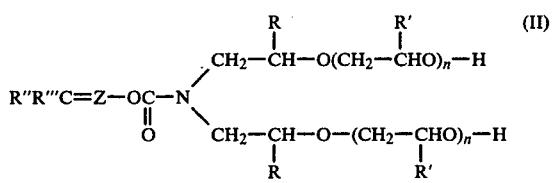

in which
Z, R, R', R", R''' and n are as defined above, and can be obtained in known manner by reacting dihydroxy carbamates corresponding to the formula

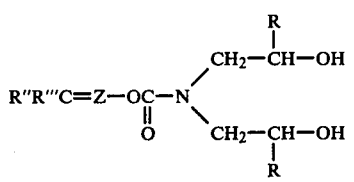

in which
Z, R, R" and R''' are as defined above, with an alkylene oxide for example, ethylene oxide, propylene oxide, butylene oxide or styrene oxide. This reaction is carried out in the absence or presence of solvents, such as dioxane or DMF and, in the presence of small quantities, preferably 0.2 to 2% by weight, of a basic catalyst such as NaOH, KOH, sodium or potassium methylate, at temperatures in the range from 50° to 180° C., preferably at temperatures in the range from 100° to 160° C. and optionally under pressure in an autoclave. Substances ranging from highly viscous to wax-like are formed and can be characterized by their degree of alkoxylation by determining the OH-number of by NMR-spectroscopy.

The unsaturated dihydroxy carbamates of formula III may be prepared for example, as follows: Preparation of

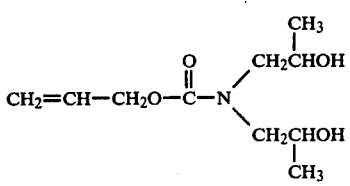

600 parts by weight of phosgene are added at 0° to −10° C. to 1000 parts by weight of toluene. 495 parts by weight of allyl alcohol are added dropwise at the aforementioned temperature, while simultaneously another 400 parts by weight of phosgene are introduced. The mixture is then stirred for 2 hours at 0° C. This is followed by stirring for another 2 to 3 hours at room temperature and under nitrogen. Nitrogen is then blown through the mixture. 2520 parts by weight of diisopropanol amine and 600 parts by weight of toluene are introduced at 0° C. The solution of the chlorocarbonic acid ester described above may be added dropwise over a period of 4 hours. After stirring for 3 hours at 0° C., the reaction mixture is finally stirred under nitrogen for 3 to 5 hours at room temperature. After the amine hydrochloride which precipitates have been filtered off under suction, the filtrate is concentrated. After the solvent has been distilled off, the required compound is distilled in a high vacuum.
Bp : 136°–141° C. 0.05 mm Hg
Yield: 75–80% of the theoretical. Preparation of

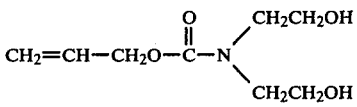

40,000 parts by volume of toluene are introduced into a 100 liter capacity enamel vessel and cooled to 0° C. 13,800 parts by weight of phosgene are then introduced at that temperature. 10,500 parts by weight of allyl alcohol are then added dropwise and, at the same time, 6,000 parts by weight of phosgene are introduced at 0° to −5° C. The reaction is exothermic. The reaction mixture is then stirred for about another 15 hours without cooling, after which time nitrogen is introduced for 5 hours through a gas inlet pipe in order to remove the excess phosgene. The contents of the vessel are cooled to 0° C., followed by the dropwise addition with thorough stirring over a period of 2 to 3 hours at 0° to −5° C., of a solution of 18,900 parts by weight of diethanolamine, 7600 parts by weight of NaOH pellets in 3000 parts by volume of water. On completion of the addition, the mixture is stirred for about another 15 hours without cooling. The aqueous phase and the organic phase are separated. The aqueous phase is concentrated to dryness under a pressure of 10 mm Hg. 30,000 parts by volume of methanol are added to the salt-containing syrupy residue. The mixture is then stirred for 2 hours at room temperature. The salts are then filtered off through a suction filter, followed by washing with 3×1000 parts by volume of methanol. The filter residue is discarded and the filtrate concentrated in vacuo. The required compound is obtained at 220° C./0.05 Torr. The organic phase is concentrated in vacuo, the required compound again being left behind as residue. As indicated above, it can be distilled. Yield: 80% of the theoretical.

Other corresponding dihydroxy carbamates can be similarly obtained.

These dihydroxy carbamates may be sulphonated with commercial-grade bisulphite liquors or with bisulphite liquors which may be freshly prepared by introducing $SO_2$ into the corresponding aqueous ammonium or alkali metal hydroxide solution. The bisulphites usable are known in the art.

The addition reaction may be carried out at temperatures of up to 100° C. preferably −10° C. to 70° C., and most preferably at room temperature, by introducing the unsaturated diols or their aqueous solutions into or slowly adding them dropwise to the bisulphite liquor. The molar ratio of bisulphite to diol should be in the range from 1:1 to 5:1, preferably in the range from 1.1:1 to 2:1. Catalysts suitable for the reaction include air, oxygen or oxygen from oxygen-yielding compounds, for example, $H_2O_2$, the oxygen having to be present in the reaction mixture in as fine a state of dispersion as possible, which state can readily be achieved by means of suitable stirrers. A high yield of sulphonate depends upon the pH-value of the reaction solution which should be in the range from pH 3 to pH 9, the range from pH 5 to pH 8 being preferred and a pH-value around 7 being particularly preferred. The required pH-value is adjusted by adding the necessary quantity of ammonia or alkali liquor, for example, to the bisulphite solution. During the reaction, the pH-value increases. However, the pH-value is kept at the required value by simultaneously adding dilute acid or by introducing more sulphur dioxide. The reaction is complete when there is no further change in the pH-value. Heat is given off during the reaction, and if desired, the reaction mixture may be cooled.

In cases where unsaturated hydroxyl-group-containing carbamates having a relatively high degree of alkoxylation are reacted, it is advisable to initially introduce the unsaturated compound, followed by dropwise addition of an excess of the bisulphite solution, again under reaction conditions described above.

Separation of most of the inorganic salts is preferably carried out by concentrating the solution to approximately half its volume and filtering the crystals percipitated. The required reaction products can be separated off from the residual inorganic salts by extraction with acetone, acetone/water mixtures, chlorinated hydrocarbons, alcohols and with alcohol/water mixtures. The sulphonates are obtained in analytically pure form in yields of up to 90%.

The dihydroxy carbamates containing sulphonic acid groups produced in accordance with the invention are eminently suitable for use a comonomers for the production of acid-modified polyurethanes, and after they have been reacted, for example, with chloroacetic acid (esters), also for the production of acid-modified polyamides. In addition, the more highly ethoxylated and/or propoxylated derivatives, optionally after reaction with isocyanates to form diurethanes, represent excellent antistatic agents and are used as additives in the production of polyacrylonitrile or polyamide sheets, films and filaments having antistatic properties.

EXAMPLE 1

Ethoxylated N,N-diethanol carbamic acid allyl ester

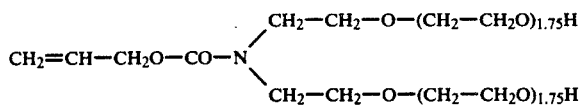

945 g (5 mol) of N,N-diethanol carbamic acid allyl ester were reacted with 880 g (20 mols) of ethylene oxide in an autoclave at 90 to 100° C. following the addition of 9.45 g of sodium as catalyst. The ethylene oxide was introduced in such a way that an internal pressure of approximately 1 atm was maintained throughout the reaction. After the ethylene oxide had been added, the reaction mixture was stirred until the excess pressure had disappeared.

Determination of the content of OH-groups produced a figure, 10.23 OH %, which corresponds to a molecular weight of 332 and a total ethylene oxide content of 2 n=3.5.

EXAMPLE 2

Propoxylated N,N-diethanol carbamic acid allyl ester

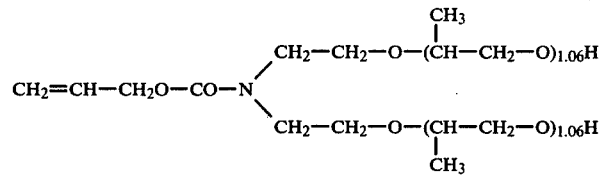

As in Example 1, 756 g (4 mol) of diethanol carbamic acid allyl ester were reacted with 580 g (10 mol) of propylene oxide in an autoclave at 140° to 150° C. in the presence of 1% of sodium as catalyst. Determination of the content of OH-groups produced a figure of 10.9 OH %, corresponding to a molecular weight of 312 and a total propylene oxide content of 2 n=2.12.

EXAMPLE 3

Sulphonate corresponding to the formula

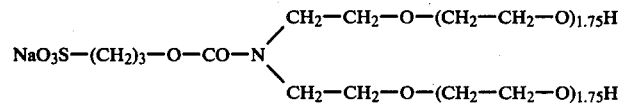

832.5 g (2.5 mol) of the diol ethoxylated in accordance with Example 1 were dissolved in 2 liters of water, followed by the addition of 650 g (2.5 mol) of a 40% sodium bisulphite solution adjusted to pH 7.1 with dilute sodium hydroxide solution. The reaction was initiated by blowing in air through a glass frit, the beginning of the reaction being indicated by an increase in the temperature to 35°-38° C. and by a rise in the pH-value. The pH-value was kept at 7—7.1 by the addition of dilute $H_2SO_4$. The end of the reaction was reached when the pH-value remained constant. The aqueous, neutral solution was concentrated to dryness and the sulphonate extracted with methanol. The ethoxylated sulphonate obtained is a pale yellow, highly viscous substance. Yield: 830 g (76% of the theoretical)

| Analysis: | C% | H% | S% | Na% |
|---|---|---|---|---|
| Calculated: | 40.4 | 6.3 | 7.2 | 5.2 |
| Found: | 40.0 | 6.5 | 7.1 | 5.2 |

EXAMPLE 4

Sulphonate corresponding to the formula

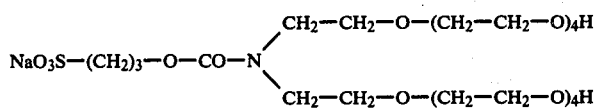

As in Example 3, 541 g (1 mol) of ethoxylated diethanol carbamic acid allyl ester with a degree of ethoxylation of 2n=8 were dissolved in 1.5 liters of water. 260 g (1 mol) of 40% sodium bisulphite solution were then added dropwise in the presence of air at a pH-value of 7.0 to 7.1 which was kept constant during the reaction by the addition of dilute $H_2SO_4$. On completion of the reaction, the required compound could be isolated by concentrating the aqueous solution to dryness, followed by extraction with methylene chloride. Yield: 575 g (89% of the theoretical).

EXAMPLE 5

Sulphonate corresponding to the formula

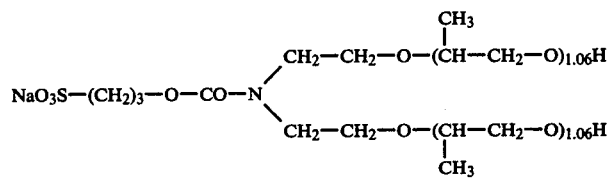

312 g (1 mol) of propoxylated N,N-diethanol carbamic acid allyl ester, prepared as in Example 2, were dissolved in 2 liters of water. 260 g (1 mol) of 40% sodium bisulphite solution were than added dropwise in the presence of air at a pH-value which was kept constant at 7.0 to 7.1. After the aqueous solution had been concentrated to dryness, the required compound could be extracted with methanol. Yield: 320 g (77% of the theoretical).

EXAMPLE 6

Sulphonate corresponding to the formula

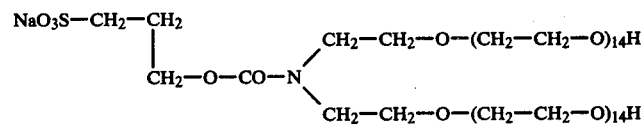

As in Example 1, 189 g (1 mol) of N,N-diethanol carbamic acid allyl ester were reacted with 1320 g (30 mol) of ethylene oxide in an autoclave at 90° to 100° C. in the presence of 1% of sodium as catalyst. Determination of the content of OH groups produced a figure of 2.39 OH %, corresponding to a molecular weight of 1421 and to a total ethylene oxide content of n=28.

710.5 g (0.5 mol) of this ethoxylated diol were dissolved in 2 liters of water, followed by the addition of 130 g (0.5 mol) of a 40% sodium bisulphite solution adjusted to pH 7.1 with dilute sodium hydroxide solution. The reaction was initiated by blowing in air through a glass frit, producing an increase in temperature to 35+-38° C. and an appreciable rise in the pH-value. The pH-value was kept at 7.0 to 7.1 by the addition of dilute $H_2SO_4$. On completion of the reaction, the aqueous neutral solution was concentrated to dryness and the sulphonate extracted with chloroform. Yield: 1280 g (84% of the theoretical.)

What is claimed is:

1. Dihydroxy carbamates containing sulphonic acid groups corresponding to the formula

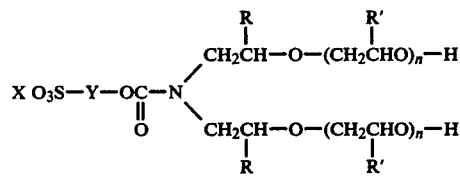

in which

Y— represents a linear or branched $C_3$-$C_6$ alkylene radical,

R,R' — represent hydrogen, $C_1$-$C_4$-alkyl or phenyl,

X — represents $NH_4$ or an alkali metal and n — is 0 or a number from 1 to 30.

2. Dihydroxy carbamates containing sulphonic acid groups, as claimed in claim 1 in which Y is —$CH_2$—$CH_2$—$CH_2$—.

* * * * *